US009675630B2

(12) United States Patent
Schmitz et al.

(10) Patent No.: US 9,675,630 B2
(45) Date of Patent: Jun. 13, 2017

(54) COMPOSITIONS AND METHODS OF USE OF A-TYPE PROCYANIDINS

(75) Inventors: Harold H. Schmitz, Bethesda, MD (US); Catherine L. Kwik-Uribe, Stroudsburg, PA (US); Mark A. Kelm, East Stroudsburg, PA (US); John F. Hammerstone, Jr., Nazareth, PA (US)

(73) Assignee: MARS, INCORPORATED, McLean, VA (US)

( * ) Notice: Subject to any disclaimer, the term of this patent is extended or adjusted under 35 U.S.C. 154(b) by 652 days.

(21) Appl. No.: 11/045,648

(22) Filed: Jan. 28, 2005

(65) Prior Publication Data

US 2005/0164956 A1 Jul. 28, 2005

Related U.S. Application Data

(60) Provisional application No. 60/539,689, filed on Jan. 28, 2004.

(51) Int. Cl.
*A61K 31/353* (2006.01)
*A61K 31/7048* (2006.01)

(52) U.S. Cl.
CPC ........ *A61K 31/7048* (2013.01); *A61K 31/353* (2013.01); *A23G 2200/04* (2013.01)

(58) Field of Classification Search
USPC ....................................................... 514/183
See application file for complete search history.

(56) References Cited

U.S. PATENT DOCUMENTS

| | | | | |
|---|---|---|---|---|
| 4,863,956 | A | 9/1989 | Gabetta et al. | 514/453 |
| 5,554,645 | A | 9/1996 | Romanczyk, Jr. et al. | 514/453 |
| 6,297,273 | B1 | 10/2001 | Romanczyk, Jr. | 514/456 |
| 6,429,202 | B1 | 8/2002 | Bombardelli et al. | 514/78 |
| 6,608,102 | B1 | 8/2003 | Howell et al. | 514/456 |
| 6,805,883 | B2 | 10/2004 | Chevaux | |
| 7,122,574 | B2 * | 10/2006 | Romanczyk et al. | 514/456 |
| 2004/0162338 | A1 * | 8/2004 | Schmitz | 514/456 |

FOREIGN PATENT DOCUMENTS

| | | |
|---|---|---|
| JP | H08-059463 | 3/1996 |
| JP | 11246562 A2 | 9/1999 |
| JP | 2003-252745 | 9/2003 |
| JP | 2003-252780 | 9/2003 |
| WO | 97-36497 | 10/1997 |
| WO | 98-09533 | 3/1998 |
| WO | WO/99/45797 | 9/1999 |
| WO | 01-78529 | 10/2001 |

OTHER PUBLICATIONS

Taddei et al., Mechanisms of Endothelial Dysfunction: Clinical Significance and Preventive Non-Pharmacological Therapeutic Strategies, 2003, Current Pharmaceutical Design, vol. 9, pp. 2385-2402.*

Hammerstone et al., Procyanidin Content and Variation in Some Commonly Consumed Foods, 2000, The Journal of Nutrition, vol. 130, pp. 2086S-2092S.*
Rat and Mouse Veterinarian Database, http://www.rmca.org/Vets/index.php?action=list, accessed Aug. 26, 2010.*
Schnackenberg et al., Two-Week Administration of Tempol Attenuates Both Hypertension and Renal Excretion of 8-ISO Prostaglandin F2alpha, 1999, Hypertension, vol. 33, pp. 424-428.*
Bruyne et al., Bioloigcal Evaluation of Proanthocyanidin Dimers and Related Polyphenols, 1999, J. Nat. Prod., vol. 62, pp. 954-958.*
Borghi et al., Use of statins and blood pressure control in treated hypertensive patients with hypercholesterolemia, 2000, J Cardiovasc Pharmacol, vol. 35 (4), pp. 549-555, Abstract Only.*
Ho, K.Y., et al., Antioxidant Activity of Tannin Components from *Vaccinium vitis*-idea L., *Pharm Pharmacol.* 51:1075-1078 (1999).
Kolodziej, et al., Moderate Cytotoxicity of Proanthocyanidins to Human Tumour Cell Lines, *Phytotherapy Research* 9:410-415 (1995).
Hartisch, Claude, et al., Dual Inhibitory Activites of Tannins from *Hamamelis virginiana* and Related Polyphenols on 5-Lipoxygenase and Lyso-PAF:Acetyl-CoA Acetyltransferase, *Planta Medica* 63:106-110.
DeBruyne, Tess, et al., Biological Evaluation of Proanthocyanidin Dimers and Related Polyphenols, *J. Nat. Prod.* 62:954-958 (1999).
Morimoto, Satoshi, et al., Tannins and Related Compounds. XXXV. Proanthocyanidins With a Doubly Linked Unit from the Root Bark of Cinnamomum Sieboldii Meisner, *Chem. Pharm. Bull.* 33:4338-4345.
Balde, A.M., et al., Dimeric and T rimeric Proanthocyanidins Possessing a Doubly Linked Structure from Pavetta Owariensis, *Phytochemistry.* 30(12):4129-4135 (1991).
Lou, Hongxiang, et al., A-Type Proanthocyanidins from Peanut Skins, *Phytochemistry* 51:297-308.
Kondo, Kazunari, et al., Conversion of Procyanidin B-Tpe (Catechin Dimer) to A-Type: Evidence for Abstraction of C-2 Hydrogen in Catechin During Radical Oxidation, *Tetrahedron Letters* 41:485-488.
Ferreira, et al., Oligomeric Proanthocyanidins: Naturally Occurring O-Heterocycles, *Nat. Prod. Rep.* 19:517-541 (2002).
Lazurus, S., et al., High-Performance Liquid Chromatography/Mass Spectrometry Analysis of Proanthocyanidins in Foods and Beverages, *J. Agric. Food Chem.* 47:3693-3701 (1999).
Karchesy, J., et al., Condensed Tannins: (4β→8;2β→O→7)-Linked Procyanidins in *Arachis hypogca* L., *J. Aric. Food Chem.* 34:966-970 (1986).

(Continued)

*Primary Examiner* — James D Anderson
*Assistant Examiner* — Meghan Finn
(74) *Attorney, Agent, or Firm* — Nath, Goldberg & Meyer; Scott H. Blackman (57) ABSTRACT

The invention relates to compositions, such as pharmaceuticals, foods, food additives, or dietary supplements, containing A-type procyanidins, and methods of use thereof, for prophylactic or therapeutic treatment of a human or a veterinary animal to treat or prevent NO-responsive health conditions, treat hypertension, cardiovascular disease, coronary artery disease and/or vascular circulation disorders, prevent or reduce the risk of heart attack, stroke, congestive heart failure and/or kidney failure, or to improve blood flow, for example renal blood flow. The composition may optionally contain an additional NO modulating agent and/or a cardiovascular-protective or therapeutic agent, or may be administered in combination with such an agent.

6 Claims, 3 Drawing Sheets

(56) References Cited

OTHER PUBLICATIONS

Balde, A.M., et al., Plant Antiviral Agents. VII. Antiviral and Antibacterial Proanthocyanidins from the Bark of Pavetta Owariensis, *Phytotherapy Research*. 4:182-188 (1990).
Lin, Lie-Chwen, et al., Immunomodulatory Proanthocyanidins from Ecdysanthera utilis, *J. Nat. Prod.* 65:505-508 (2002).
Montenegro de Matta, S., Alkaloids and Procyanidins of an Uncaria Sp. From Peru, *Il. Farmaco. Ed. Sc.* 31(7):527-535 (1975).
Foo et al., A-Type Proanthocyanidin Trimers from Cranberry that inhibit Adherence of Uropathogenic P-Fimbriated *Escherichia coli*, *J. Nat. Prod.* 63:1225-1228 (2000).
Prior, Ronald L., Identification of Procyanidins and Anthocyanins in Blueberries and Cranberries (*Vaccinium* Spp) Using High-Performance Liquid Chromatography/Mass Spectrometry, *J. Agric. Food Chem.* 49:1270-76.
Kashiwada et al., *Antitumor Agents, Tannins and Related Compounds as Selective Cytotoxic Agents*.
Maher, M. A. et al., Cranberry juice induces nitric oxide-dependent vasodilation in vitro and its infusion transiently reduces blood pressure in anesthetized rats, 2000, J. Med. Food. 3 (3):141-7.
Reed, J., Cranberry flavonoids, atherosclerosis and cardiovascular health, 2002, Crit. Rev. Food Sci. Nutr., 42 (3 Suppl):301-16.
Kiderle, A. F. et al., Tannins and Related Compounds: Killing of Amastigotes of Leishmania donovani and Release of Nitric Oxide and Tumour Necrosis Factor alpha in Macrophages in vitro, Z. Naturforsch. 56c, 444-454 (2001).
Kerwin, J. F. et al., Nitric Oxide: A new paradigm for second messengers, Journal of Medicinal Chemistry, 1995, 38 (22):4343-4362.
Tikkanen, I. et al., Nitric oxide in hypertension and renal diseases, Annals of Medicine, 1995, 27(3):353-357.

\* cited by examiner

Figure 2. Platelet aggregation (a), P/M (b) and P/N (c) measured in response to all concentrations collagen (0.125, 0.25 and 0.5μg/ml) in the absence and presence of a range of flavanols or ASA (100μM). Results = mean ± S.E.M. n=9 determinations. *p<0.05 cf control, $p<0.05 cf ASA.

Figure 3. Platelet aggregation (a), P/M (b), P/N (c), CD62P-M (d), CD62P-N (e), CD11b-M (f) and CD11b-N (g) measured in response to all concentrations collagen (0.125, 0.25 and 0.5μg/ml) in the absence and presence of a range of flavanols and ASA (100μM). Results = mean ± S.E.M. n=9 determinations. *p<0.05 cf control, $p<0.05 cf ASA.

COMPOSITIONS AND METHODS OF USE OF A-TYPE PROCYANIDINS

This application claims the benefit, under 35 USC Section 119, of the U.S. Provisional Appl. No. 60/539,689 filed Jan. 28, 2004, the disclosure of which is hereby incorporated herein by reference.

FIELD OF THE INVENTION

The invention relates to compositions containing A-type procyanidins, and methods of use thereof, for prophylactic or therapeutic treatment of a human or a veterinary animal.

BACKGROUND OF THE INVENTION

Polyphenols are an incredibly diverse group of compounds (Ferriera et al., Tetrahedron, 48: 10, 1743-1803, 1992). They widely occur in a variety of plants, some of which enter into the food chain. In some cases they represent an important class of compounds for the human diet. Although some of the polyphenols are considered to be non-nutritive, interest in these compounds has arisen because of their possible beneficial effects on health. For instance, quercetin (a flavonoid) has been shown to possess anticarcinogenic activity in experimental animal studies (Deshner et al., Carcinogenesis, 7: 1193-1196, 1991: and Kato et al., Carcinogenesis, 4, 1301-1305 1983). (+)-catechin and (−)-epicatechin (flavan-3-ols) have been shown to inhibit Leukemia virus reverse transcriptase activity (Chu et al., J. of Natural Prod., 55: 2, 179-183, 1992). Nobotanin (an oligomeric hydrolyzable tannin) has also been shown to possess anti-tumor activity (Okuda et al., presented at the XVIth International Conference of the Groupe Polyphenols, Lisbon, Portugal, Jul. 13-16, 1992). Procyanidin oligomers have been reported by the Kikkoman Corporation for use as antimutagens (JP 04190774A, Jul. 7, 1992).

Some polyphenol, such as B-type procyanidins have been shown to have a beneficial effect on nitric oxide (NO) release and hence on treatment of a variety of health conditions that positively respond to NO (see e.g. U.S. Pat. No. 6,670,390 to Romanczyk et al.).

Nitric oxide (NO) is known to inhibit platelet aggregation, monocyte adhesion and chemotaxis, and proliferation of vascular smooth muscle tissue which are critically involved in the process of atherogenesis. The concentration of NO can be reduced in atherosclerotic tissues due to its reaction with oxygen free radicals. The loss of NO due to these reactions leads to increased platelet and inflammatory cell adhesion to vessel walls to further impair NO mechanisms of relaxation. In this manner, the loss of NO may promote atherogenic processes, leading to progressive disease states.

Hypertension is a condition where the pressure of blood as it circulates within the blood vessels is higher than normal. When the systolic pressure exceeds 150 mm Hg or the diastolic pressure exceeds 90 mm Hg for a sustained period of time, damage is done to the body. Hypertension is a leading cause of vascular diseases, including stroke, heart attack, heart failure, and kidney failure. For example, excessive systolic pressure can rupture blood vessels anywhere. In cases when a rapture occurs within the brain, a stroke results. Hypertension can also cause thickening and narrowing of the blood vessels which can lead to atherosclerosis. Elevated blood pressure can also force the heart muscle to enlarge as it works harder to overcome the elevated resting (diastolic) pressure when blood is expelled. This enlargement can eventually produce irregular heart beats or heart failure. Hypertension is called the "silent killer" because it causes no symptoms and can only be detected when blood pressure is checked.

The regulation of blood pressure is a complex event where one mechanism involves the expression of constitutive Ca+2/calmodulin dependent form of nitric oxide synthase (NOS), known as endothelial nitric oxide synthase or eNOS. NO produced by this enzyme produces smooth muscle relaxation in the vessel (dilation), which lowers the blood pressure. When circulating concentrations of NO are reduced, either because production is blocked by an inhibitor or in pathological states, such as atherosclerosis, the vascular muscles do not relax to the appropriate degree. The resulting vasoconstriction increases blood pressure and may be responsible for some forms of hypertension.

Given the large number of people suffering from hypertension and related diseases and disorders of the vascular system, there is considerable interest in finding therapeutic ways to maintain the NO pool at its normal, healthy levels. Pharmacological agents capable of releasing NO, such as nitroglycerin or isosorbide dinitrate, remain mainstays of vasorelaxant therapy. Applicants have now surprisingly discovered that A-type procyanidins can be utilized for preserving the NO pool, inducing vasorelaxation and/or treating and/or preventing NO-responsive diseases and disorders.

SUMMARY OF THE INVENTION

The invention relates to compositions containing A-type procyanidins, and methods of use thereof, for prophylactic or therapeutic treatment of a human or a veterinary animal.

In one aspect, the invention relates to a composition, such as a pharmaceutical, a food, a food additive, or a dietary supplement comprising an effective amount of an A-type procyanidin. The composition may optionally contain an additional NO modulating agent and/or a cardiovascular-protective or therapeutic agent, or may be administered in combination with such an agent. Also within the scope of the invention are packaged products containing the above-mentioned compositions and a label and/or instructions for use to treat or prevent NO-responsive health conditions, treat hypertension, cardiovascular disease, coronary artery disease and/or vascular circulation disorders, prevent or reduce the risk of heart attack, stroke, congestive heart failure and/or kidney failure, or to improve blood flow, for example renal blood flow.

In another aspect the invention relates to methods of use of A-type procyanidins to treat or prevent NO-responsive health conditions, treat hypertension, cardiovascular disease, coronary artery disease and/or vascular circulation disorders, prevent or reduce the risk of heart attack, stroke, congestive heart failure and/or kidney failure, or to improve blood flow, for example renal blood flow.

BRIEF DESCRIPTION OF THE DRAWINGS

FIG. 1A-C represents dose-dependent relaxation mediated by A-type procyanidins in pre-contracted aortic rings: A) A2 dimer; B) A1 dimer; and C) A-type trimer.

FIG. 2A-C represents the results of platelet aggregation experiments with A1 dimer.

FIG. 3-G represents the results of platelet aggregation experiments with A1 dimer.

DETAILED DESCRIPTION

All patents, patent applications and references cited in this application are hereby incorporated herein by reference. In case of any inconsistency, the present disclosure governs.

The invention relates to compositions comprising an effective amount of an A-type procyanidin, or a pharmaceutically acceptable salt or derivative thereof.

The A-type procyanidin of the present invention is an oligomer composed of n monomeric, flavan-3-ol units of the formula:

(i) the monomeric units are connected via interflavan linkages 4→6 and/or 4→8;
(ii) at least two of the monomeric units are additionally linked by an A-type interflavan linkage (4→8; 2→O→7) or (4→6; 2→O→7); and
(iii) n is 2 to 12.

It will be understood by a person of skill in the art that one of the two flavanol units linked by the A-type interflavanoid linkage must comprise two bonds at the 2- and 4-positions. Both of these have either α or β stereochemistry, i.e., the bonds are either 2α, 4α or 2β, 4β. These bonds connect to the 6- and 7-O-positions, or the 8- and 7-O-positions of the second flavanol unit linked by the A-type interflavan linkage. In constituent flavanol units of the oligomer which do not comprise A-type interflavan linkages at positions C-2 and C-4, the linkage at position C-4 can have either alpha or beta stereochemistry. The OH group at position C-3 of flavanol units has either alpha or beta stereochemistry. Flavan-3-ol (monomeric) units may be (+)-catechin, (−)-epicatechin and their respective epimers (e.g. (−)-catechin and (+)-epicatechin)).

An A-type procyanidin as defined above may be derivatized, for instance esterified, at one or more of the OH groups on one or more of the constituent flavan-3-ol units. A given flavan-3-ol unit may thus comprise one or more ester groups, preferably gallate ester groups, at one or more of the 3-, 5-, 7-, 3'- and 4'-ring positions. It may in particular be a mono-, di-, tri-, tetra- or penta-gallated unit.

Examples of the compounds useful for products, and in the methods of the present invention, include the compounds wherein the integer n is 3 to 12; 4 to 12; 5 to 12; 4 to 10; or 5 to 10. In some embodiments, n is 2 to 4, or 2 to 5, for example n is 2 or 3.

In one embodiment, the A-type procyanidin is epicatechin-(4β→8; 2β→O→7)-catechin (i.e., A1 dimer), or a pharmaceutically acceptable salt or derivative thereof, and has the following formula:

In another embodiment, the A-type procyanidin is epicatechin-(4β→8; 2β→O→7)-epicatechin (i.e., A2 dimer) and has the following formula:

In yet another embodiment, the A-type procyanidin is an A-type trimer and has the following formula:

A-type procyanidins may be of natural origin or synthetically prepared. For example, A-type procyanidins may be isolated from peanut skins as described in Example 1, or as described in Lou et al., Phytochemistry, 51: 297-308 (1999), or Karchesy and Hemingway, *J. Agric. Food Chem.*, 34: 966-970 (1986), the relevant portions of each being hereby incorporated herein by reference. Mature red peanut skin contain about 17% by weight procyanidins, and among the dimeric procyanidins epicatechin-(4β→8; 2β→O→7)-catechin dominates, with smaller proportion of epicatechin-(4β→8; 2β→O→7)-epicatechin being present. However, in addition to procyanidins having (4→8; 2→O→7) double linkages, procyanidins having (4→6; 2→O→7) double linkages are also found in peanut skins.

Other sources of the above compounds are cranberries as described, for example in Foo et al., *J. Nat. Prod.*, 63: 1225-1228, and in Prior et al., *J Agricultural Food Chem.*, 49(3): 1270-76 (2001), the relevant portions of each being hereby incorporated herein by reference. Other sources include *Ecdysanthera utilis* (Lie-Chwen et al., *J. Nat. Prod.*, 65: 505-8 (2002)) and *Aesculus hippocastanum* (U.S. Pat. No. 4,863,956), the relevant portions of each being hereby incorporated herein by reference.

A-type compounds may also be obtained from B-type procyanidins via oxidation using 1,1-diphenyl-2-pycrylhydrazyl (DPPH) radicals under neutral conditions as described in Kondo et al., *Tetrahedron Lett.*, 41: 485 (2000), the relevant portions of which are hereby incorporated herein by reference. Methods of obtaining natural and synthetic B-type procyanidins are well known in the art and are described, for example, in U.S. Pat. No. 6,670,390 to Romanczyk et al.; U.S. Pat. No. 6,207,842 to Romanczyk et al.; U.S. Pat. No. 6,420,572 to Romanczyk et al.; and U.S. Pat. No. 6,156,912 to Romanczyk et al.

The A-type procyanidins may be used in the compositions described herein and administered in the form of an extract (e.g. peanut skins extract) comprising A-type procyanidins as the main component.

The A-type procyanidins may be isolated and purified, i.e., they are separated from compounds with which they naturally occur (if the A-type procyanidin is of natural origin), or they are synthetically prepared, in either case such that the level of contaminating compounds (impurities) does not significantly contribute to, or detract from, the effectiveness of the A-type procyanidin. For example, an isolated and purified A1 dimer is separated from A2 dimer, with which it may occur in nature, to the extent achievable by the available commercially viable purification and separation techniques.

The compounds may be substantially pure, i.e., they possess the highest degree of homogeneity achievable by the available purification, separation and/or synthesis technology. As used herein, a "substantially pure A1 dimer" is separated from A2 dimer to the extent technologically and commercially possible, and a "substantially pure A-type trimer" is separated from other A-type oligomers (to the extent technologically and commercially possible) but may contain a mixture of several A-type trimers. In other words, the phrase "isolated and purified trimer" refers primarily to one trimer, while a "substantially pure trimer" may encompass a mixture of trimers.

In some embodiments, the A-type procyanidins are at least 80% pure, preferably at least 85% pure, at least 90% pure, at least 95% pure, at least 98% pure, or at least 99% pure. Such compounds are particularly suitable for pharmaceutical applications.

Methods of Use

Any compound described in the application may be used to practice the methods described herein. As shown in Example 3, A-type procyanidins affect the nitric oxide (NO) pathway in endothelial cells helping preserve the NO pool. Without being bound by theory, the NO pool is preserved by inducing NO synthesis and/or decreasing NO degradation. The compounds also cause vasorelaxation of constricted blood vessels. They may also be used for anti-platelet therapy as shown in Example 4.

Thus, the invention relates to a method of treating or preventing an NO-responsive disease or disorder by administering to a subject in need thereof an effective amount of an A-type procyanidin oligomer composed of n monomeric, flavan-3-ol units of the formula:

(i) the monomeric units are connected via interflavan linkages 4→6 and/or 4→8;
(ii) at least two of the monomeric units are additionally linked by an A-type interflavan linkage (4→8; 2→O→7) or (4→6; 2→O→7);
(iii) n is 2 to 12;
or a pharmaceutically acceptable salt or derivative thereof, and wherein the subject is a human or a veterinary animal.

The A-type procyanidins may be isolated and purified or substantially pure. In some embodiments, the above compounds may be at least about 80% pure, at least about 85% pure, at least about 90% pure, at least 95% pure or at least 98% pure. Examples of the compounds for use in the above method include the compounds wherein the integer n is 3 to 12; 4 to 12; 5 to 12; 4 to 10; or 5 to 10. In some embodiments, n is 2 to 4, or 2 to 5, for example n is 2 or 3.

As used herein, an "NO-responsive disease or disorder" refers to a health condition which responds to treatment with NO. Examples of such conditions include, but are not limited to, NO-mediated or NO-dependent diseases and disorders, in which the pathology of the disease/disorder is caused by abnormal functioning of the NO pathway. Preferably the conditions include hypertension, cardiovascular disease, coronary artery disease and/or vascular circulation disorders, heart attack, stroke, congestive heart failure, kidney failure, and renal disease. The A-type procyanidins may be administered alone or in combination with another cardiovascular therapeutic agent.

Because high blood pressure increases the risk of heart attack, stroke, congestive heart failure, and kidney failure, A-type procyanidins which cause vasorelaxation can be utilized, alone or in combination with other cardiovascular-protective agents, to prevent these conditions. Particularly suitable subjects include subjects with high blood pressure in combination with diabetes, obesity, high cholesterol levels and/or smokers, in which patients the risk of heart attack and stroke increases several times.

As used herein, "treatment" means improving an existing medical condition, such as cardiovascular disease, for example by slowing down the disease progression, prolonging survival, reducing the risk of death, and/or providing a measurable improvement of disease parameters.

The term "preventing" means reducing the risks associated with developing a disease, including reducing the onset of the disease.

As used herein, the terms "cardiovascular-protective or therapeutic agent" refers to an agent other than A-type procyanidin which is effective to treat or protect cardiovascular system. Examples of such agents are anti-platelet therapy agents (e.g. COX inhibitors, such as aspirin; B-type procyanidins); NO-modulating agents, cholesterol reducing agents (e.g. sterol, stanol).

In some embodiments, the invention relates to the following methods:

A method of treating or preventing an NO-responsive disease or disorder by administering to a subject in need thereof an effective amount of epicatechin-(4β→8; 2β→O→7)-catechin (i.e., A1 dimer) of the following formula, or a pharmaceutically acceptable salt or derivative thereof:

wherein the subject is a human or a veterinary animal. The A1 dimer may be isolated and purified. In some embodiments, the above compound may be at least about 90% pure, at least 95% pure or at least 98% pure.

A method of treating or preventing an NO-responsive disease or disorder by administering to a subject in need thereof an effective amount of epicatechin-(4β→8; 2β→O→7)-epicatechin (i.e., A2 dimer) of the following formula, or a pharmaceutically acceptable salt or derivative thereof:

wherein the subject is a human or a veterinary animal. The A2 dimer may be isolated and purified. In some embodiments, the above compound may be at least about 90% pure, at least 95% pure or at least 98% pure.

A method of treating or preventing an NO-responsive disease or disorder by administering to a subject in need thereof an effective amount of an A-type trimer of the following formula, or a pharmaceutically acceptable salt or derivative thereof:

wherein the subject is a human or a veterinary animal. The A-type trimer may be isolated and purified, or substantially pure. In some embodiments, the above compounds may be at least about 80% pure, at least about 85% pure, at least about 90% pure, at least 95% pure or at least 98% pure.

In certain embodiment, the invention provides for the following exemplary methods:

A method of treating hypertension by administering to a subject in need thereof an effective amount of an A-type procyanidin oligomer composed of n monomeric, flavan-3-ol units of the formula, or a pharmaceutically acceptable salt or derivative thereof:

(i) the monomeric units are connected via interflavan linkages 4→6 and/or 4→8;
(ii) at least two of the monomeric units are additionally linked by an A-type interflavan linkage (4→8; 2→O→7) or (4→6; 2→O→7);
(iii) n is 2 to 12;
and wherein the subject is a human or a veterinary animal.

The A-type procyanidins may be isolated and purified or substantially pure. In some embodiments, the above compounds may be at least about 80% pure, at least about 85% pure, at least about 90% pure, at least 95% pure or at least 98% pure.

Examples of the compounds for use in the above method include the compounds wherein the integer n is 3 to 12; 4 to 12; 5 to 12; 4 to 10; or 5 to 10. In some embodiments, n is 2 to 4, or 2 to 5, for example n is 2 or 3.

In certain embodiments, the invention includes the following exemplary methods:

A method of treating hypertension by administering to a subject in need thereof an effective amount of epicatechin-(4β→8; 2β→O→7)-catechin (i.e., A1 dimer) of the formula, or a pharmaceutically acceptable salt or derivative thereof:

wherein the subject is a human or a veterinary animal. The A1 dimer may be isolated and purified. In some embodiments, the above compound may be at least about 90% pure, at least 95% pure or at least 98% pure.

A method of treating hypertension by administering to a subject in need thereof an effective amount of epicatechin-(4→8; 2β→O→7)-epicatechin (i.e., A2 dimer) of the following formula, or a pharmaceutically acceptable salt or derivative thereof:

wherein the subject is a human or a veterinary animal. The A2 dimer may be isolated and purified. In some embodiments, the above compound may be at least about 90% pure, at least 95% pure or at least 98% pure.

A method of treating hypertension by administering to a subject in need thereof an effective amount of A-type trimer of the following formula, or a pharmaceutically acceptable salt or derivative thereof:

wherein the subject is a human or a veterinary animal. The A-type procyanidin trimer may be isolated and purified or substantially pure. In some embodiments, the above compounds may be at least about 80% pure, at least about 85% pure, at least about 90% pure, at least 95% pure or at least 98% pure.

Also within the scope of the invention are methods of improving/treating erectile dysfunction in a person in need thereof using any of the compounds recited herein.

The effective amount for use in the above methods may be determined by a person of skill in the art using the guidance provided herein and general knowledge in the art. For example, the effective amount may be such as to achieve a physiologically relevant concentration in the body (e.g. blood) of a mammal. Such a physiologically relevant concentration may be at least about 10 nanomolar (nM), preferably at least about 20 nM, or at least about 100 nM, and more preferably at least about 500 nM. In one embodiment, at least about one micromole in the blood of the mammal, such as a human, is achieved. The compounds of formula $A_n$, as defined herein, may be administered at from about 50 mg/day to about 1000 mg/day, preferably from about 100-150 mg/day to about 900 mg/day, and most preferably from about 300 mg/day to about 500 mg/day. However, amounts higher than stated above may be used.

The compounds may be administered acutely, or treatments/preventive administration may be continued as a regimen, i.e., for an effective period of time, e.g., daily, monthly, bimonthly, biannually, annually, or in some other regimen, as determined by the skilled medical practitioner for such time as is necessary. The administration may be continued for at least a period of time required to exhibit therapeutic/prophylactic effects. Preferably, the composition is administered daily, most preferably two or three times a day, for example, morning and evening to maintain the levels of the effective compounds in the body of the mammal. To obtain the most beneficial results, the composition may be administered for at least about 30, or at least about 60 days. These regiments may be repeated periodically.

Compositions and Formulations

The compounds of the invention may be administered as a pharmaceutical, food, food additive or a dietary supplement.

As used herein a "food" is a material consisting essentially of protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993. The term food includes a beverage adapted for human or animal consumption. As used herein a "food additive" is as defined by the FDA in 21 C.F.R. 170.3(e)(1) and includes direct and indirect additives. As used herein, a "pharmaceutical" is a medicinal drug. See Merriam-Webster's Collegiate Dictionary, 10th Edition, 1993. A pharmaceutical may also be referred to as a medicament. As used herein, a "dietary supplement" is a product (other than tobacco) that is intended to supplement the diet that bears or contains the one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients.

Pharmaceuticals containing the inventive compounds, optionally in combination with another cardiovascular-protective or therapeutic agent, may be administered in a variety of ways such as orally, sublingually, bucally, nasally, rectally, intravenously, parenterally and topically. A person of skill in the art will be able to determine a suitable mode of administration to maximize the delivery of A-type procyanidins, optionally in combination with another cardiovascular-protective or therapeutic agent. Thus, dosage forms adapted for each type of administration are within the scope of the invention and include solid, liquid and semi-solid dosage forms, such as tablets, capsules, gelatin capsules (gelcaps), bulk or unit dose powders or granules, emulsions, suspensions, pastes, creams, gels, foams, jellies or injection dosage forms. Sustained-release dosage forms are also within the scope of the invention and may be prepared as described in U.S. Pat. Nos. 5,024,843; 5,091,190; 5,082,668; 4,612,008 and 4,327,725, relevant portions of which are hereby incorporated herein by reference. Suitable pharmaceutically acceptable carriers, diluents, or excipients are generally known in the art and can be determined readily by a person skilled in the art. The tablet, for example, may comprise an effective amount of the A-type procyanidin containing composition and optionally a carrier, such as sorbitol, lactose, cellulose, or dicalcium phosphate.

The dietary supplement containing A-type procyanidins, and optionally another cardiovascular-protective or therapeutic agent, may be prepared using methods known in the art and may comprise, for example, nutrient such as dicalcium phosphate, magnesium stearate, calcium nitrate, vitamins, and minerals.

Further within the scope of the invention is an article of manufacture such as a packaged product comprising the composition of the invention (e.g. a food, a dietary supplement, a pharmaceutical) and a label indicating the presence of, or an enhanced content of the inventive compounds or directing use of the composition for methods described herein.

Also within the scope of the invention is an article of manufacture (such as a packaged product or kit) adapted for use in combination therapy comprising at least one container and at least one A-type procyanidin, or a pharmaceutically acceptable salt or derivatives thereof. The article of manufacture further comprises at least one additional agent, a cardiovascular-protective or therapeutic agent (i.e., other than the A-type procyanidin, or a pharmaceutically acceptable salt or derivative thereof), which agent may be provided as a separate composition, in a separate container, or in admixture with the compound of the invention.

As described above, cardiovascular-protective or therapeutic agents are effective to treat or protect cardiovascular system. Examples of such agents are anti-platelet therapy agents (e.g. COX inhibitors, such as aspirin); NO-modulating agents, cholesterol reducing agents (e.g. sterol, stanol).

In certain embodiments, cardiovascular-protective or therapeutic agents optionally administered with A-type procyanidins may be B-type procyanidins, for example cocoa flavanols and/or procyanidins as described below.

The B-type polyphenols for use in the present invention may be of natural origin, for example, derived from a cocoa bean or another natural source of polyphenols, or prepared synthetically. For example, the B-type procyanidins and their derivatives are those described in U.S. Pat. No. 6,670,390 to Romanczyk et al., the relevant portions of which are hereby incorporated herein by reference. A person of skill in the art may select natural or synthetic polyphenol based on availability or cost. Polyphenols may be included in the composition in the form of a cocoa ingredient containing cocoa polyphenols, for example, chocolate liquor included in chocolate, or may be added independently of cocoa ingredients, for example, as an extract, extract fraction, isolated and purified individual compound, pooled extract fractions or a synthetically prepared compound.

The term "cocoa ingredient" refers to a cocoa solids-containing material derived from shell-free cocoa nibs such as chocolate liquor and partially or fully-defatted cocoa solids (e.g. cake or powder).

The B-type procyanidin oligomers may have from 2 to about 18, preferably from 2 to about 12, and most preferably from 2 to about 10 monomeric units. Alternatively, the oligomers may have from 3-18, preferably 3-12, and more preferably 3-10 monomeric units; or from 5-18, preferably 5-12 and more preferably 5-10 monomeric units. For example, oligomers may be dimers, trimers, tetramers, pentamers, hexamers, heptamers, octamers, nonamers and decamers. In the oligomer, monomers are connected via interflavan linkages of (4→6) and/or (4→8). Oligomers with exclusively (4→8) linkages are linear; while the presence of at least one (4→6) bond results in a branched oligomer. Also within the scope of the invention are oligomers comprising at least one non-natural linkage (6→6), (6→8), and (8→8). The synthesis of such non-naturally occurring oligomers is described in the International Appl. No. PCT/US00/08234 published on Oct. 19, 2000 as WO 00/61547, the relevant portions of which are hereby incorporated herein by reference.

The B-type procyanidins may be prepared by extraction from cocoa beans, cocoa nibs, or cocoa ingredients such as chocolate liquor, partially defatted cocoa solids, and/or fully defatted cocoa solids. Preferably, the extract is prepared from a fully or partially defatted cocoa powder. Beans from any species of *Theobroma, Herrania* or inter- and intra-species crosses thereof may be used. The extract may be prepared from fermented, underfermented or unfermented beans, the fermented beans having the least amount of cocoa polyphenols and the unfermented the most. The selection of beans may be made based on the fermentation factor of the beans, for example, the extract may be made from the beans having a fermentation factor of about 275 or less. Optimizing the level of polyphenols in the cocoa ingredient and extract thereof by manipulating the degree of fermentation may be done as described in the International Appl. No. PCT/US97/15893 published as WO98/09533, the relevant portions of which are hereby incorporated herein by reference.

Cocoa polyphenols may be extracted from cocoa ingredients that have been processed using traditional methods of cocoa processing (described, for example, in Industrial Chocolate Manufacture and Use, ed. Beckett, S. T., Blackie Acad. & Professional, New York, 1997, such as in Chapters 1, 5 and 6) or using an improved processing method described in U.S. Pat. No. 6,015,913 to Kealey et al. that preserves polyphenols (by preventing their destruction) in cocoa ingredients in contrast to the traditional methods. The improved cocoa processing method omits the traditional roasting step. Thus, cocoa ingredients obtainable by (a) heating the cocoa bean for a time and a temperature sufficient to loosen the cocoa shell without roasting the cocoa nib; (b) winnowing the cocoa nib from the cocoa shell; (c) screw pressing the cocoa nib and (d) recovering the cocoa butter and partially defatted cocoa solids which contain preserved levels of cocoa polyphenols, may be used. The method retains a much higher level of higher procyanidin oligomers than traditional processing methods. Cocoa solids produced by this method may contain greater than 20,000 µg of total flavanol and/or procyanidins per gram nonfat solids; preferably greater than 25,000 µg/g, more preferably greater than 28,000 µg/g, and most preferably greater than 30,000 µg/g. For purposes of this invention, the total flavanol and/or procyanidin amounts are determined as described in Example 2.

B-type procyanidins may be extracted from the sources indicated above, or any other polyphenol or flavanol or procyanidin containing source, using solvents in which the polyphenols dissolve. Suitable solvents include water or organic solvent such as methanol, ethanol, acetone, isopropyl alcohol and ethyl acetate. Solvent mixtures may also be used. When water is used as the solvent, it may be slightly acidified, for example with acetic acid. Examples of some solvents are mixtures of water and organic solvent, for example aqueous methanol, ethanol or acetone. Aqueous organic solvents may contain, for example, from about 50% to about 95% of organic solvent. Thus, about 50%, about 60%, about 70%, about 80% and about 90% organic solvent in water may be used. The solvent may also contain a small amount of acid such as acetic acid, for example, in the amount of about 0.5% to about 1.0%. The composition of the extracts, i.e., the representation (i.e., oligomeric profile) and the amount of procyanidin oligomers, will depend on the choice of solvents. For example, the water extract contains primarily monomers, the ethyl acetate extract contains monomers and lower oligomers, mainly dimers and trimers, and the aqueous methanol, ethanol or acetone extract contains monomers and a range of higher oligomers. One of the solvents for extraction of monomer as well as higher procyanidin oligomers is about 70% acetone. However, any extract containing polyphenols is useful in the invention. The methods of cocoa polyphenol extraction are known in the art and are described, for example, in the U.S. Pat. No. 5,554,645 to Romanczyk et al. and the International Appl. No. PCT/US97/05693, published as WO97/36497. Thus, in one embodiment, the cocoa extract is prepared by reducing cocoa beans to cocoa powder, defatting the powder, extracting the cocoa polyphenols, and purifying the extract. The cocoa powder can be prepared by freeze-drying the cocoa beans and pulp, depulping and dehulling the freeze-dried cocoa beans, and grinding the dehulled beans.

The B-type cocoa polyphenol extract may be purified, for example, by removal of the caffeine and/or theobromine, and further purified by gel permeation chromatography and/or High Pressure Liquid Chromatography (HPLC). Gel permeation chromatography (e.g. on Sephadex LH-20) may be used to enrich the extract for higher procyanidin oligomers. For example, the eluate containing monomers and lower oligomers may not be collected until the oligomer(s) of choice begins eluting from the column. An example of such an extract is known in the art and is described in Example 5 of the International Appl. No. PCT/US97/05693, published as WO97/36497, the relevant portions of which are hereby incorporated by reference herein. By using preparative HPLC, for example, normal phase HPLC, the extract may be fractionated, for example, into monomeric and oligomeric fractions containing at least 50% by weight of the monomer or specific oligomer(s). When a particular fraction contains the monomers or any of the lower oligomers (e.g. dimers, trimers or tetramers fraction), the fraction contain about 90 to 95% by weight of the particular oligomeric fraction. The desired fractions may be pooled after separation to obtain a combination of oligomers of choice for example to contain oligomers 3-10 or 5-10. A person of skill in the art can manipulate the chromatographic conditions to achieve the desired procyanidin profile in view of the guidance in this specification, general knowledge in the art and, for example, the teachings of U.S. Pat. No. 5,554,645 to Romanczyk et al. and the International Appl. No. PCT/US97/05693, published as WO97/36497.

The monomeric fraction typically contains a mixture of monomers epicatechin and catechin; and the oligomeric fraction typically contains a mixture of dimers (in a dimer fraction), trimers (in a trimer fraction), tetramers (in a tetramer fraction), etc. Mixtures of monomers and oligomers occur in isolated fractions because cocoa contains more than one type of each of monomer, dimer, etc. The oligomeric variability occurs as a result of two monomers, epicatechin and catechin, that are building blocks of procyanidins, as well as the chemical bond connecting monomers in the oligomer. Thus, cocoa dimers are primarily B2 and B5, each of which contains two monomers of epicatechin. Individual monomers and oligomers may be obtained using reversed-phase HPLC, e.g. using a C18 column.

B-type cocoa polyphenol may be used in the compositions of the invention as a cocoa extract, e.g. solvent-derived extract, cocoa fraction, isolated compounds or in the form of a cocoa ingredient or a chocolate containing an effective amount of cocoa flavanols and/or procyanidins. The cocoa ingredients may be prepared using traditional cocoa processing procedures but is preferably prepared using the method described in U.S. Pat. No. 6,015,913 to Kealey et al. Alternatively, to enhance the level of cocoa polyphenols, chocolate liquor and cocoa solids prepared from cocoa beans having a fermentation factor of about 275 or less may be used. These ingredients have cocoa polyphenol content that is higher than can be obtained using traditional cocoa processing methods (e.g. with roasting) and fully fermented beans. The chocolate may be prepared using conventional techniques from the ingredients described above or using an improved process for preserving cocoa polyphenols during chocolate manufacturing as described in the International Appl. No. PCT/US99/05414 published as WO99/45788, the relevant portions of which are hereby incorporated herein by reference. A chocolate prepared by at least one of the following non-traditional processes is referred to herein as a "chocolate having a conserved amount of cocoa polyphenols": (i) preparing cocoa ingredients from underfermented or unfermented cocoa beans; (ii) preserving cocoa polyphenol during cocoa ingredient manufacturing process; and (iii) preserving cocoa polyphenol during chocolate manufacturing process.

Synthetic B-type procyanidins may also be used and are prepared by methods known in the art and as described for example in the International Appl. No. PCT/US98/21392 published as WO99/19319, the relevant portions of which are hereby incorporated herein by reference.

Flavanol and/or procyanidin derivatives may also be useful. These include esters of monomer and oligomers such as the gallate esters (e.g. epicatechin gallate and catechin gallate); compounds derivatized with a saccharide moiety such as mono- or di-saccharide moiety (e.g. β-D-glucose), glycosylated monomers and oligomers, and mixtures thereof; metabolites of the procyanidin monomers and oligomers, such as the sulphated, glucouronidated, and methylated forms except for the enzyme cleavage products of procyanidins generated by colonic microflora metabolism. The derivatives may be from natural sources or prepared synthetically.

The foods comprising A-type and/or B-type procyanidins and optionally another cardiovascular-protective/treatment agent may be adapted for human or veterinary use, and include pet foods. The food may be other than a confectionery, however, the preferred cholesterol lowering food is a confectionery such as a standard of identity (SOI) and non-SOI chocolate, such as milk, sweet and semi-sweet chocolate including dark chocolate, low fat chocolate and a candy which may be a chocolate covered candy. Other examples include a baked product (e.g. brownie, baked snack, cookie, biscuit) a condiment, a granola bar, a toffee chew, a meal replacement bar, a spread, a syrup, a powder beverage mix, a cocoa or a chocolate flavored beverage, a pudding, a rice cake, a rice mix, a savory sauce and the like. If desired, the foods may be chocolate or cocoa flavored. Food products may be chocolates and candy bars, such as granola bars, containing nuts, for example, peanuts, walnuts, almonds, and hazelnuts. It should be noted that the addition of nuts with skins to the food described herein may also increase the total polyphenol content since, for example, peanut skins contain about 17% flavanols and procyanidins and almond skins contain about 30% flavanols and procyanidins. Ground peanut skins may be added to the compositions of the invention. In one embodiment, the nut skins, e.g. peanut skins, are added to the nougat of a chocolate candy.

In certain embodiments, the non-chocolate food product contains from about at least 5 micrograms/g to about 10 mg/g, and, for example, at least 5 micrograms/g food product, preferably at least 10 microgram/g, more preferably at least 100 micrograms/g of flavanols and/or B-type procyanidins and/or A-type procyanidins. If desired, the non-chocolate food products can contain much higher levels of cocoa procyanidins than those found in the chocolate food products described below.

The chocolate confectionery may be milk or dark chocolate. In certain embodiments, the chocolate comprises at least 3,600 micrograms, preferably at least 4,000 micrograms, preferably at least 4,500 micrograms, more preferably at least 5,000 micrograms, and most preferably at least 5,500 micrograms of flavanols and/or B-type procyanidins and/or A-type procyanidins each per gram of chocolate, based on the total amount of nonfat cocoa solids in the product. In other embodiments, the chocolate contains at least 6,000 micrograms, preferably at least 6,500 micrograms, more preferably at least 7,000 micrograms, and most preferably at least 8,000 micrograms of flavanols and/or B-type procyanidins and/or A-type procyanidins per gram, and even more preferably 10,000 micrograms/g based on the nonfat cocoa solids in the product.

A milk chocolate confectionery may have at least 1,000 micrograms, preferably at least 1,250 micrograms, more preferably at least 1,500 micrograms, and most preferably at least 2,000 micrograms flavanols and/or B-type procyanidins and/or A-type procyanidins each per gram of milk chocolate, based on the total amount of nonfat cocoa solids in the milk chocolate product. In the preferred embodiment, the milk chocolate contains at least 2,500 micrograms, preferably at least 3,000 micrograms, more preferably at least 4,000 micrograms, and most preferably at least 5,000 micrograms flavanols and/or B-type procyanidins and/or A-type procyanidins each per gram of milk chocolate, based on the total amount of nonfat cocoa solids in the milk chocolate product.

L-arginine may be added to food products in the amount that can vary. Typically, cocoa contains between 1 to 1.1 grams of L-arginine per 100 grams of partially defatted cocoa solids. It can range from 0.8 to 1.5 per 100 grams of cocoa. In some embodiments, the chocolate food products of this invention contain L-arginine in an amount greater than that which naturally occurs in the cocoa ingredients. Knowing the amount of cocoa ingredients and L-arginine used in the food product, one of ordinary skill in the art can readily determine the total amount of L-arginine in the final product. The food product will generally contain at least 5 micrograms/g, preferably at least 30 micrograms/g, or at least 60 micrograms/g, even more preferably at least 200 micrograms/g food product.

A daily effective amount of flavanols and/or A-type and/or B-type procyanidins may be provided in a single serving. Thus, a confectionery (e.g. chocolate) may contain at least about 100 mg/serving (e.g. 150-200, 200-400 mg/serving).

The invention is further described in the following non-limiting examples.

EXAMPLES

Example 1

Extraction and Isolation of A-type Procyanidins

Extraction

Finely ground peanut skins (498 g) were defatted with hexane (2×2000 mL). Hexane was removed by centrifugation at ambient temperature, 5 min at 3500 rpm, and discarded. Residual hexane was allowed to evaporate overnight. The following day, defatted peanut skins were extracted for 2 hours at ambient temperature with acetone: water:acetic acid (70:29.5:0.5 v/v/v) (2×2000 mL). Extracts were recovered by centrifugation (ambient temperature, 5 min at 3500 rpm). Organic solvents were removed by rotary evaporation under partial pressure (40° C.). Aqueous portion of extraction solvent was removed by freeze drying to provide a brown-red crusty solid (51.36 g).

Gel Permeation of Crude Peanut Skin Extract

Crude peanut skin extract (24 g), obtained as described above, was dissolved in 70% methanol (150 mL), refrigerated for 1 hour, vortexed for 3 sec, then centrifuged at ambient temperature, for 5 min at 3500 rpm. The supernatant was loaded atop a large column containing Sephadex LH-20 (400 g) preswollen in methanol. Column was eluted isocratically with 100% methanol at a flow rate of 10 mL/min. Twenty nine fractions, 250 mL each, were collected and combined in accordance to their composition as determined by NP-HPLC (Adamson et al., *J. Ag. Food Chem.*, 47: 4184-4188, 1999) to give a total of eight fractions (i-viii). Fraction i contained monomers epicatechin and catechin, fraction ii-vii contained dimers, trimers or mixtures thereof. Fraction v (1.8 g) and vii (2.7 g) contained a preponderance of dimers and trimers, respectively, and were selected for further purification.

Purification of A-type Dimers and Trimers

Fraction v (1.8 g) was dissolved in 0.1% acetic acid in 20% methanol (40 mg/mL). Injection volumes were 2 mL. Separations were conducted on a Hypersil ODS (250×23 mm) under gradient conditions. Mobile phases consisted of 0.1% acetic acid in water (mobile phase A) and 0.1% acetic acid in methanol (mobile phase B). Gradient conditions were: 0-10 min, 20% B isocratic; 10-60 min, 20-40% B linear; 60-65 min, 40-100% B linear. Separations were monitored at 280 nm. Fractions with equal retention times from several preparative separations were combined, rotary evaporated at 40° C. under partial vacuum and freeze dried. Five fractions (a-e) were obtained. Fractions d and e were characterized by LCMS as dimers A1 and A2, respectively. In addition to A1 and A2 dimers, four different dimers were previously isolated from peanut skins (Lou et al., *Phytochemistry* 51, 297-308, 1999).

Fraction vii was purified as described above to obtain a single trimer with an A-linkage having the formula represented above.

The structures of purified compounds were confirmed by Mass Spectroscopy, and the purity of the compounds was determined using HPLC at UV 280 nm. A1 dimer was 95% pure, A2 dimer was 91% pure, and A trimer was 84% pure.

Example 2

Determination of Flavanols/Procyanidins

Procyanidins were quantified as follows: a composite standard was made using commercially available (−)-epicatechin, and dimers through decamers obtained in a purified state by the methods described in Hammerstone, J. F. et al., *J. Ag. Food Chem.*; 1999; 47 (10) 490-496; Lazarus, S. A. et al., *J. Ag. Food Chem.*; 1999; 47 (9); 3693-3701; and Adamson, G. E. et al., *J. Ag. Food Chem.*; 1999; 47 (10) 4184-4188. Standard Stock solutions using these compounds were analyzed using the normal-phase HPLC method described in the previously cited Adamson reference, with fluorescence detection at excitation and emission wavelengths of 276 nm and 316 nm, respectively. Peaks were grouped and their areas summed to include contributions from all isomers within any one class of oligomers and calibration curves were generated using a quadratic fit. Monomers and smaller oligomers had almost linear plots which is consistent with prior usage of linear regression to generate monomer-based and dimer-based calibration curves.

These calibration curves were then used to calculate procyanidin levels in samples prepared as follows: First, the cocoa or chocolate sample (about 8 grams) was defatted using three hexane extractions (45 mL each). Next, one gram of defatted material was extracted with 5 mL of the acetone/water/acetic acid mixture (70:29.5:0.5 v/v). The quantity of procyanidins in the defatted material was then determined by comparing the HPLC data from the samples with the calibration curves obtained as described above (which used the purified oligomers). The percentage of fat for the samples (using a one gram sample size for chocolate or one-half gram sample size for liquors) was determined using a standardized method by the Association of Official Analytical Chemists (AOAC Official Method 920.177). The quantity of total procyanidin levels in the original sample (with fat) was then calculated. Calibration was performed prior to each sample run to protect against column-to-column variations.

Example 3

Effect of A-type Procyanidins on NO Production and Vasorelaxation

The compounds obtained as described in Example 1, were investigated for their effect on nitric oxide (NO) production and vasorelaxation using serum-free human umbilical vein endothelial cell (HUVEC) culture system in vitro and rabbit aortic ring model ex vivo, respectively. NO production by endothelial cells and relaxation of pre-constricted aortic rings are two main markers for evaluating cardiovascular effects of test compounds.

In vitro Experiment

HUVECs obtained from a single donor were cultured in serum free, low protein (0.5 g/l), antibiotic-free cell culture medium supplemented with essential growth factors, nutrients and minerals. The cultured cell expressed endothelial markers (von Willebrand factor, CD31 antigen, uptake of Dil-Ac-LDL) and exhibited the typical "cobble-stone morphology" when grown to confluence. The cell culture medium was substituted with apo-transferrin, superoxide dismutase, and catalase to exclude secondary effects of test compounds involving their auto-oxidation mediated hydrogen peroxide formation.

Test compounds were evaluated with respect to their potential to acutely (2 hours) and chronically (5 doses given in a 24 h period) modulate NO production. Positive controls (acetylcholine and/or histamine) and negative control L-NNMA (NO synthase inhibitor) were included in all experiments. Cell counts and total protein were used to assess intra-assay variation. Potential toxic effects of tested compounds were also monitored (MTT reduction was measured).

NO production was evaluated by measuring the total amount of all major nitric oxide end products (NOx, including nitrate, nitrite, nitrosothiols) present in the cell culture medium. For this purpose NOx were directly reduced by vanadium(III)chloride/HCl at 95 degrees C. yielding NO. The amount of NO released from the culture medium was subsequently evaluated by measuring the chemiluminescence emitted during the stoichiometrical reaction between ozone and NO using NO Analyzer (Sievers Instruments, Inc. Boulder, Colo.).

The data presented herein were obtained from three experiments and were expressed as the concentration of NO present (in $\mu$mol/l) (as NOx) in the cell culture medium +/−standard deviation (SD). The data were corrected for the NOx intrinsically present in the fully supplemented cell culture medium and normalized with respect to the volume of media from which the ample was drawn. Data were analyzed using Student's t-test with a 95% level of confidence. P values equal to or less than 0.005 were defined as statistically significant.

For the acute effect test, HUVECs were incubated with a single dose of A2 dimer and A-type trimer for 2 and 24 hours at concentrations of 100 nM, 1 $\mu$M, and 10 $\mu$M at 37 C and 5% $CO_2$. No effect was observed on NO production after 2 hours. After 24 hours following a single dose, no effect was seen at 1 $\mu$M concentration. Both test compounds increased NO production above the control level at concentration of 10 $\mu$M (of the two, A2 performed better) but neither to statistically significant levels. Based on the MTT assay, the test compounds did not have toxic effects.

For the chronic effect test, HUVECs were incubated with 5 subsequent doses of test compounds, each for 24 hours. After each 24 hour treatment, culture medium was replaced. A2 dimer and A-type trimer were tested. A-type trimer exhibited statistically significant increase in NO production (p=0.041).

Ex Vivo Experiment

Effect of A-type procyanidins on endothelium-dependent relaxation was tested in an ex vivo experiment performed as previously described by Karim et al., *J. Nutrl Suppl.*, 130 (8S): 2105S-2108S (2000), the relevant portions of which are hereby incorporated herein by reference. The advantage of using this method is that it assesses functional cardiovascular end points. The method is only able to assess acute events and does not allow for the identification of drug-induced protein expression/activity.

In summary, rabbit aortic rings were obtained from male New Zealand White rabbits. Following isolation, the rings were mounted in oxygenated Kreb's buffer, and pre-constricted with NE ($10^{-6}$ M). When the tension had reached a steady state, cumulative concentrations of the test compounds were applied (10-9 to 10-4 M).

A positive control acetylcholine ($10^{-6}$M) and a negative control L-NAME were included in the experiment. Use of L-NAME, which is a NO synthase (NOS) inhibitor, allows for differentiating between endothelium dependent and endothelium independent relaxation events. Denuding of aortic rings represent a similar control. 400 U/mL of catalase was added into the aortic bath prior to the addition of each of the test compounds to ensure that the observed effects are not caused by hydrogen peroxide ($H_2O_2$) generation in the culture medium. The relaxation response was measured as a function of the decrease in the tension (g) exerted by the aortic rings over time. Data obtained were expressed as a percent relaxation of the norepinephrine (NE) constricted rings. The same statistical approach as described above was used. Dose response curves were obtained by plotting the average percent relaxation (+/−SE) against the concentrations used.

The results of the ex vivo screening demonstrates that both A1 and A2 dimers and A-type trimer induced vasorelaxation at a concentration of $10^{-4}$M: at that concentration A1 dimer induced 93.20$^{+}$/−3.46% vasorelaxation, A2 dimer induced 85.00$^{+}$/−2.91% vasorelaxation, and A-type trimer induced 56.5$^{+}$/−16.56% relaxation. Moreover, both A1 and A2 dimers were more potent relaxants that the positive control (acetylcholine) and that difference was statistically significant at p=0.005 for A1 dimer.

The relaxation responses were attenuated when the vessels were either denuded or pre-treated with L-NAME. Acetylcholine typically produced a relaxation response at a concentration of $10^{-7}$M, reaching maximal relaxation at a concentration of $10^{-6}$M. No response was observed when vessels were treated with vehicle alone.

Figure 1:
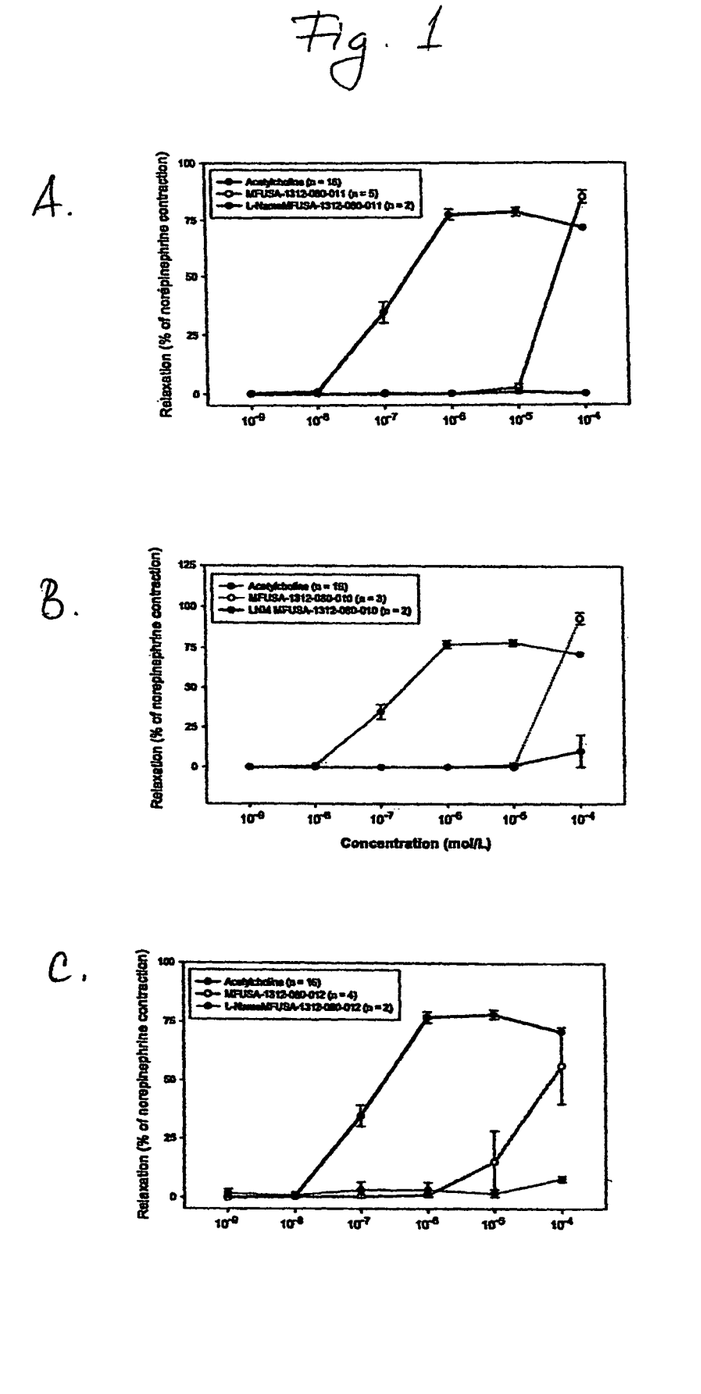

Dose dependent relaxation mediated by the test compounds is represented in FIGS. 1A-C.

Example 4

Effects of A1 Dimer on Platelet in Whole Blood

Platelet aggregation of A1 dimer [A1D] was measured using a platelet counting technique, and formation of platelet/monocyte conjugates (P/M) and platelet/neutrophil conjugates (P/N) by flow cytometry. In later experiments the activation state of platelets associated with leukocytes (CD62P) was also measured and also the activation state of the leukocytes themselves (CD11b).

Materials and Methods

A1 dimer [A1D] was dissolved in ethanol. Once in solution, further dilution with saline was possible. Hirudin, (Revasc™) was obtained from Novartis (Basel, Switzerland) and was stored as a 5 mg/ml solution in saline in a glass vial at −20° C. Collagen (Nycomed) was from Axis Shield Diagnostics (Dundee, UK). Concentrations were prepared from the stock solution (1 mg/ml) using the isotonic glucose buffer supplied by the manufacturer. Aspirin (acetyl salicylic acid-ASA), adenosine diphosphate (ADP), platelet activating factor (PAF), arachidonic acid (AA) and epinephrine were from Sigma. Fixing solution consisted of 140 mM NaCl containing 0.16% w/v formaldehyde, 4.6 mM $Na_2EDTA$, 4.5 mM $Na_2HPO4$ and 1.6 mM $KH_2PO4$, pH 7.4.

Blood samples were studied using the Multi-Sample Agitator (MSA) produced by the Medical Engineering Unit (University of Nottingham). The MSA is used to maintain blood samples at 37° C. and to agitate small samples of blood at a stir speed of 1,000 rpm as required.

Flow cytometry was carried out using commercially available fluorescent labelled antibodies on a Facscan (Becton Dickinson, UK) equipped with a 5W laser operating at 15 mW power and a wavelength of 488 nM or an LSRII flow cytometer (Becton Dickinson, UK) equipped with an additional red Trigon laser operating at a wavelength of 633 nM.

Blood Collection

Blood was obtained from healthy volunteers, who denied taking any aspirin or NSAIDS in the previous 10 days. This blood was dispensed into graduated polystyrene tubes that contained hirudin (final concentration 50 μg/ml) and a small volume of the flavanol under investigation or ethanol as control. The final concentration of ethanol in the blood was always 0.3%. In some experiments, aspirin (ASA) or saline as control was also included in the tube. The tubes were then capped and inverted three times to ensure adequate mixing then placed in the MSA at 37° C. for 30 min before the experiments were performed, during which time the blood was left undisturbed. A further sample of blood was taken into a commercially prepared vacutainer tube that contained $K_2EDTA$ as anticoagulant.

Platelet Aggregation

Following the 30 min pre-incubation, aliquots of blood (480 μl) were dispensed into small polystyrene tubes each containing a stir bar and stirred for 2 min in the MSA. After 2 min a solution (20 μl) of agonist or vehicle control were added to the tubes. These were then stirred in the MSA for up to 10 min at which time the platelet aggregates were fixed by mixing a small sub sample with fixative solution in a 1:2 ratio (v/v). The platelet count in the fixed samples was determined using the UltraFlo-100 Whole Blood Platelet Counter. Platelet aggregation was calculated as the percentage loss of single platelets with reference to the platelet count of the EDTA sample.

Platelet-Leukocyte Conjugate Formation

Platelet-leukocyte conjugate formation was measured in the same stirred samples used to measure platelet aggregation. Sub samples were taken 4 min or 10 min following the addition of agonist and transferred into the appropriate antibody or antibody mixture. These were then incubated in the dark at room temperature for not less than 20 min. Following red cell lysis and a washing procedure the cell suspensions were applied to either the FACScan or the LSRII flow cytometer. Leukocytes were identified by logical gating from dot plots of forward scatter (cell size) and side scatter (cell granularity) profiles acquired with linear amplification. Monocytes were identified by their forward scatter-side scatter profile and CD14 (PE) positivity, while neutrophils were identified in the same way but were negative for CD14 expression. The "pan" leukocyte marker, CD45 (PerCP) was also used to identify the leukocyte population. Fluorescence parameters were acquired with logarithmic amplification. Platelet monocyte (P/M) and platelet neutrophil (P/N) conjugates were quantified as median CD42a (FITC) fluorescence of the monocyte (P/M mf) or neutrophil population (P/N mf). Leukocyte activation was measured by CD11b (AlexaFluor647) expression (CD11b-M for monocytes and CD11b-N for neutrophils). Platelet activation (P-selectin expression) was measured by CD62P (PE) positivity of the platelets associated with leukocytes as (CD62P-M on P/M and CD62P-N on P/N).

The FACScan was used to measure the fluorescent probes in experiments where three colours were used together, but the LSRII was needed in order to study four colours. The LSRII is a more sensitive machine and produces higher fluorescence values (mf) than the FACScan. Results obtained on the FACScan cannot be directly compared with the results obtained on the LSRII.

Results

Effects of A1 Dimer on Aggregation, P/M and P/N

Blood was obtained from three different volunteers and the platelet aggregation and platelet/leukocyte conjugate formation was measured in response to collagen (0, 0.125, 0.25 and 0.5 µg/ml). In these experiments aspirin was used at a concentration of 100 µM and A1 dimer was used at 0.3 mM. Aggregation was measured at 4 and 10 min following agonist addition and platelet/leukocyte conjugate formation only at 10 min.

Figure 2:
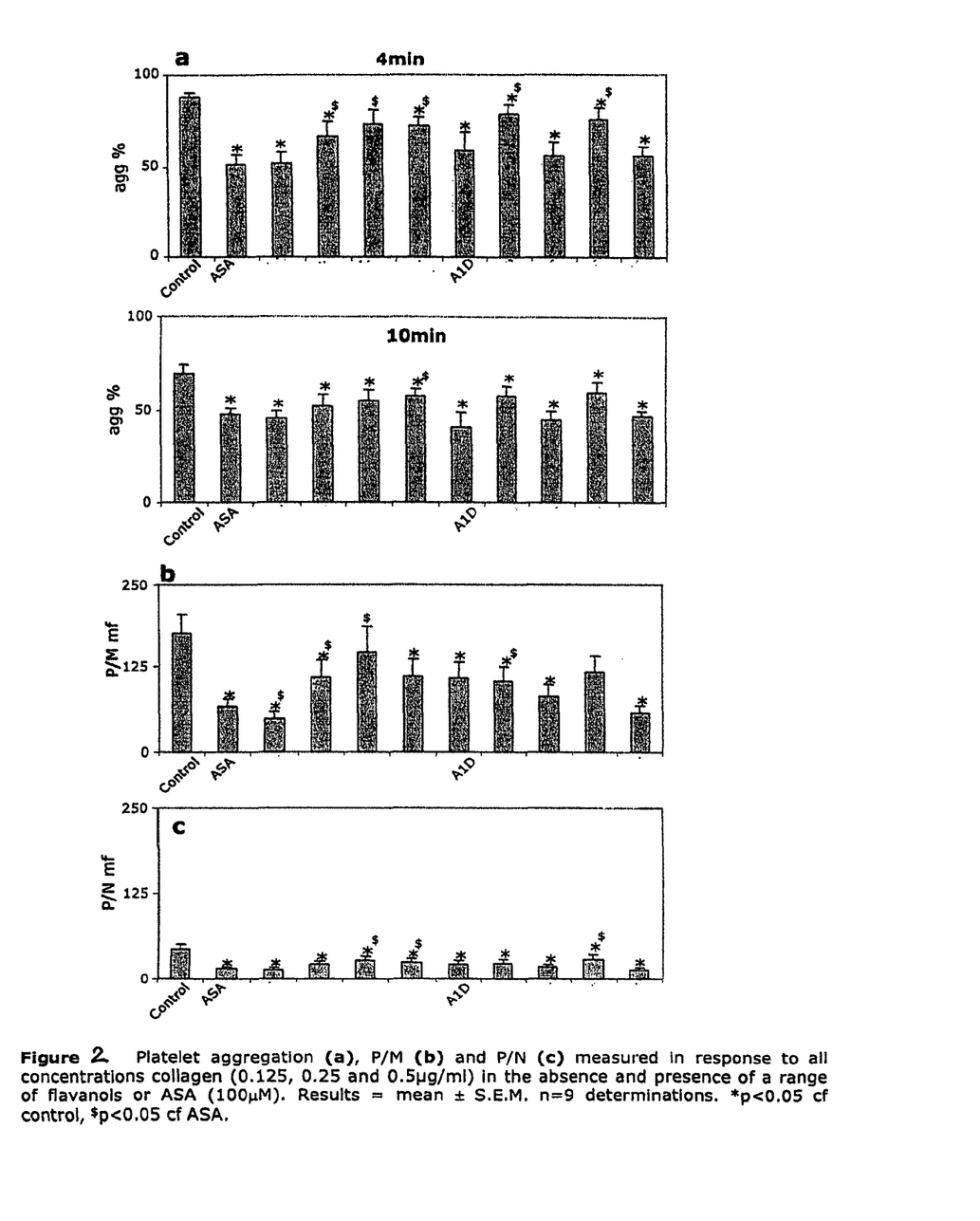

The absolute response of the blood from the different volunteers to collagen varied. This meant that the relative inhibitory effects of a flavanol was dependent on the volunteer's responsiveness to the particular collagen concentration used. For this reason it was decided that an appropriate means of analysing the results, for comparative purposes, would be to calculate the mean values for A1 dimer irrespective of the collagen concentration used. The results are shown in FIG. 2. (Certain compounds other than A-type procyanidins were also tested in these experiment, however, since they are not relevant to the discussion here, they were not identified.) Because, for each of the three blood samples three concentrations of collagen were used, the results are each the means (±sem) of nine individual values.

A1 dimer inhibited collagen-induced platelet aggregation. ASA control also effectively inhibited the aggregation, P/M and P/N.

From this point on it was decided to include measures of the extent of the activation of both platelets and leukocytes in the conjugates that formed following addition of collagen to blood. P-selectin (CD62P) was measured on the platelets associated with leukocytes in the conjugates that formed. Leukocyte activation was measured as the amount of CD11b that was expressed. Four-colour analysis was used.

Figure 3:
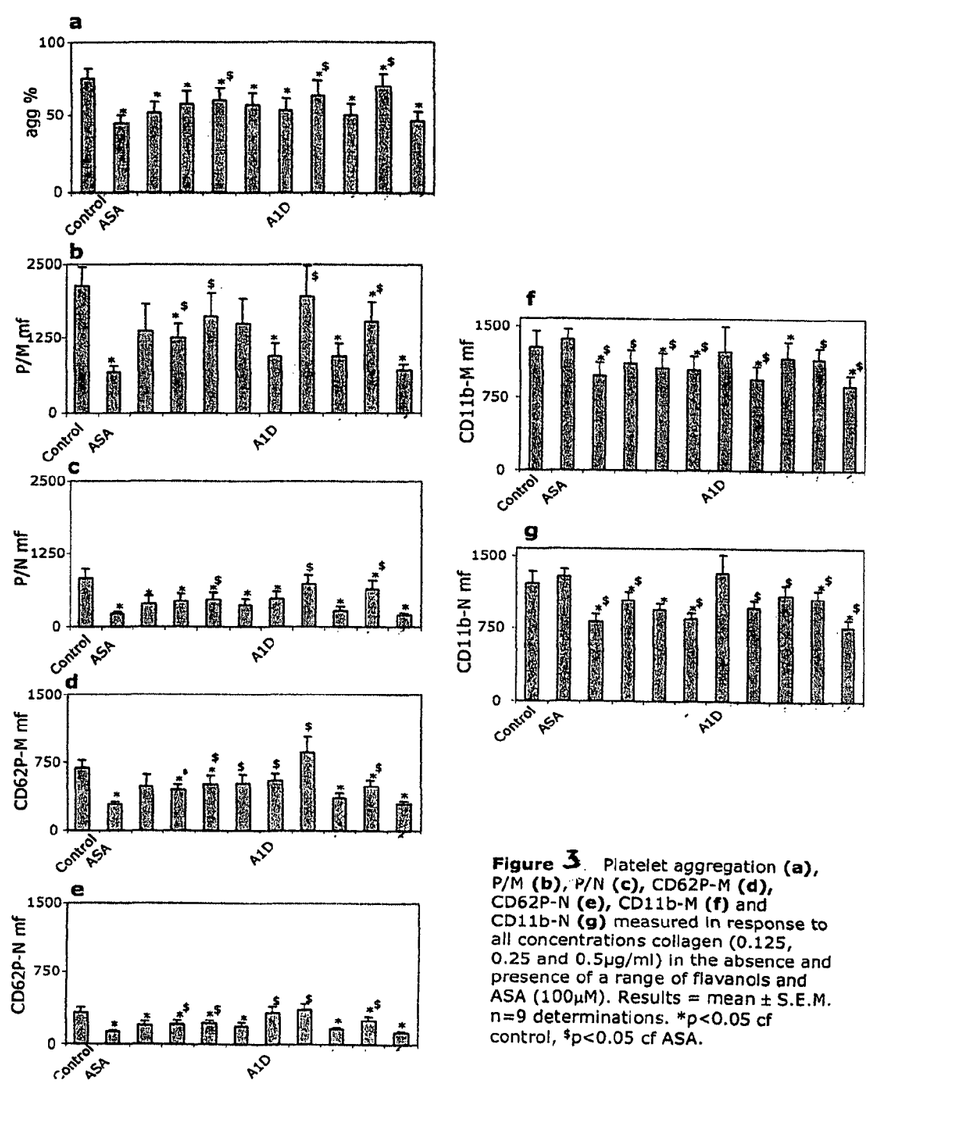

Comparison of the Effects of Flavanols on Collagen-Induced Aggregation, P/M, P/N, CD62P-M, CD62P-N, CD11b-M and CD11b-N Blood was obtained from three different volunteers and the platelet aggregation (4 min) and platelet/leukocyte conjugate formation (10 min) was measured in response to collagen (0, 0.125, 0.25 and 0.5 µg/ml). At the same time the activation of platelets and leukocytes in the conjugates were measured by incubation with CD62P and CD11b antibodies. In these experiments aspirin was used at a concentration of 100 µM and A1 dimer was used at 0.3 mM. The results are shown in FIG. 3. (Certain compounds other than A-type procyanidins were also tested in this experiment, however, since they are not relevant to the discussion here, they were not identified.) As before, the analysis was performed by including all results for all three collagen concentrations and calculating the mean (±sem, n=9).

A1 dimer inhibited collagen induced aggregation. However, it was noteworthy that A1D did not inhibit leukocyte activation (CD11b on monocytes and leukocytes). Aspirin also had no effect on CD11b.

What is claimed is:

1. A method of inducing vasorelaxation in a subject suffering from hypertension comprising administering to the subject, as a regimen, a composition consisting of an effective amount to induce vasorelaxation of an A-type procyanidin composed of n monomeric units of the formula:

wherein
(i) the monomeric units are connected via interflavan linkages 4→6 and/or 4→8;
(ii) at least two of the monomeric units are additionally linked by an A-type interflavan linkage (4→8; 2→O→7) or (4→6; 2→O→7);
(iii) n is 3;
or a pharmaceutically acceptable salt thereof,
and wherein the subject is a human.

2. The method of claim 1, wherein the A-type trimer is substantially pure.

3. The method of claim 1, wherein the A-type trimer has the formula:

4. A method of treating hypertension by inducing vasorelaxation comprising administering to a subject in need thereof a composition consisting of an effective amount to induce vasorelaxation of an A-type procyanidin composed of n monomeric units of the formula:

wherein
(i) the monomeric units are connected via interflavan linkages 4→6 and/or 4→8;
(ii) at least two of the monomeric units are additionally linked by an A-type interflavan linkage (4→8; 2→O→7) or (4→6; 2→O→7);
(iii) n is 3;
or a pharmaceutically acceptable salt thereof,
and wherein the subject is a human.

5. The method of claim 4, wherein the A-type trimer is substantially pure.

6. The method of claim 4, wherein the A-type trimer has the formula:

* * * * *